(12) United States Patent
Hvarre Christensen

US008658206B2

(10) Patent No.: US 8,658,206 B2
(45) Date of Patent: Feb. 25, 2014

(54) COMPOSITIONS COMPRISING STRONTIUM AND VITAMIN D AND USES THEREOF

(75) Inventor: John N. Hvarre Christensen, Koege (DK)

(73) Assignee: Mokwalo SA, Luxembourg (LU)

( * ) Notice: Subject to any disclaimer, the term of this patent is extended or adjusted under 35 U.S.C. 154(b) by 341 days.

(21) Appl. No.: 11/570,767

(22) PCT Filed: Jun. 24, 2005

(86) PCT No.: PCT/DK2005/000425
§ 371 (c)(1),
(2), (4) Date: May 8, 2007

(87) PCT Pub. No.: WO2006/000224
PCT Pub. Date: Jan. 5, 2006

(65) Prior Publication Data
US 2008/0026037 A1 Jan. 31, 2008

(30) Foreign Application Priority Data
Jun. 25, 2004 (DK) ................................ 2004 00991
Nov. 10, 2004 (DK) ................................ 2004 01733

(51) Int. Cl.
A61K 33/24 (2006.01)
A61K 31/28 (2006.01)
A61K 9/00 (2006.01)
A61K 9/28 (2006.01)
A61K 31/59 (2006.01)
A61P 19/00 (2006.01)

(52) U.S. Cl.
USPC ............ 424/464; 424/600; 514/167; 514/492

(58) Field of Classification Search
None
See application file for complete search history.

(56) References Cited

U.S. PATENT DOCUMENTS

| | | | | |
|---|---|---|---|---|
| 3,345,265 | A * | 10/1967 | Grodberg et. al. | 424/475 |
| 3,699,221 | A * | 10/1972 | Schole et al. | 424/54 |
| 3,988,434 | A | 10/1976 | Schole et al. | |
| 4,939,164 | A | 7/1990 | Wierzbicki et al. | |
| 5,075,336 | A * | 12/1991 | Czernecki et al. | 514/574 |
| 5,128,367 | A | 7/1992 | Wierzbicki et al. | |
| 5,380,530 | A | 1/1995 | Hill | |
| 5,624,906 | A * | 4/1997 | Vermeer | 514/23 |
| 5,856,356 | A | 1/1999 | Tsouderos et al. | |
| 2004/0059134 | A1 | 3/2004 | Vaysse-Ludot et al. | |
| 2004/0059135 | A1 | 3/2004 | Vaysse-Ludot et al. | |
| 2004/0063972 | A1 | 4/2004 | Vaysse-Ludot et al. | |
| 2006/0275503 | A1 * | 12/2006 | Hansen et al. | 424/617 |

FOREIGN PATENT DOCUMENTS

| | | |
|---|---|---|
| CN | 1342653 | 4/2002 |
| WO | WO-2004 098617 | 11/2004 |
| WO | WO-2004 098618 | 11/2004 |
| WO | WO-2004 098619 | 11/2004 |

OTHER PUBLICATIONS

Gorlick et al., "Biology of Childhood Osteogenic Sarcoma and Potential Targets for Therapeutic Development: Meeting Summary." Clinical Cancer Research 2003:9;5442-5453.*
Chapuy: "Prevention and Treatment of Osteoporosis" Aging Clin. Exp. Res., vol. 7, 1995, 1995 pp. 164-173.
Reginster J-Y et al. Strontium Ranelate: A New Paradigm in the Treatment of Osteoporosis: Drugs of Today/Medicamentos de Actualidad, J.R. Prous SS.A International Publishers, ES, vol. 39, No. 2, Feb. 1, 2003, pp. 89-101.
Sorbera L A et al. "Strontium Ranelate Treatment and Prevention of Osteoporosis Bone Resorption Inhibitor Bine Formation Stimulant" Drugs of ther Future, Barcelona, ES, vol. 28, No. 4, Apr. 1, 2003, pp. 328-335.
Cohen-Solal M. Strontium overload and toxicity: impact on renal osteodystrophy. Nephrol Dial Transplant 2002; 17 Suppl 2:30-4.
Dahl SG, Allain P, Marie PJ, Mauras Y, Bolvin G, Ammann P, Tsouderos Y, Delmas PD Christiansen C. Incorporation and distribution of strontium in bone. Bone. Apr. 2001;28(4):446-53.
Reginster JY, Deroisy R, Dougados M, Jupsin I, Colette J, Roux C. Prevention of early postmenopausal bone loss by strontium ranelate: the randomized two-year, double-masked, dose-ranging, placebo-controlled PREVOS trial, Osteoporos Int. Dec. 2002; 13(12):925-31.
Cabrera WE, Schrooten I, De Broe ME, D'Haese PC 1. J Bone Miner Res. May 1999; 14(5):661-8. Strontium and bone.
Grynpas MD, Marie PJ, Effects of low doses of strontium on bone quality and quantity in rats. Bone. 1990; 11(5):313-9.
Verberckmos SC, De Broe ME, D'Haese PC. Dose-dependent effects of strontium on osteoblast function and mineralization. Kidney Int. Aug. 2003; 64(2):553-43.
Sips Aj, van der Vijgh WJ, Barto R, Netelenbos JC. Intestinal absorption of strontium chloride in healthy volunteers: pharmacokinetics and reproducibility. Br J Clin Pharmacol. Jun. 1996;41(6):543-9.
Marie PJ, Ammann P, Bolvin G, Rey C Mechanisms of action and therapeutic potential of strontium in bone. Calcif Tissue Int Sep. 2001;69(3):121-9.
Boivin, G. et al., Strontium Distribution and Interactions with Bone Mineral in Monkey Iliac Bone After Strontium Salt (S 12911) Administration, *Journ of Bone and Mineral Research*, 11:1302-1311, 1996.
Burguera M. et al., "Age and sex-related calcium and strontium concentrations in different types of human bones," *Trace Elements and Electrolytes*, 19: 143-151, 2002.
Christoffersen J. et al., "Effects of Strontium Ions on Growth and Dissolution of Hydroxyapatite and on Bone Mineral Detection," *Bone*, 20:47-54, 1997.

(Continued)

*Primary Examiner* — Walter Webb
(74) *Attorney, Agent, or Firm* — Gifford, Krass, Sprinkle, Anderson & Citkowski, P.C.

(57) ABSTRACT

The invention relates to the finding that very favorable pharmacokinetic characters are obtained by combining two strontium salts in one pharmaceutical composition. The present invention relates in one aspect to a pharmaceutical composition comprising at least two strontium salts for use as a medicament, and in particular for the treatment and prevention of bone disorders such as osteoporosis. The composition preferably comprises strontium carbonate and strontium chlorides. Further included may be a vitamin D compound, preferably vitamin $D_3$.

22 Claims, 1 Drawing Sheet

(56) References Cited

OTHER PUBLICATIONS

Communication from patentee to EPO—response to Com 96(2) EPC filed Jan. 18, 2008.
Creger C.R. et al., "Strontium and Bone Development Under Conditions of Suboptimal Vitamin D," *Calc. Tiss. Tes.*, 8: 83-86, 1971.
Ferraro Eugene F. et al., "The Effect of Strontium Chloride Upon Alveolar Bone," *J Periodontol*, 51:345-347, 1980.
Marie, P. et al., Histomorphometry of Bone Changes in Stable Strontium Therapy, *Proceedings of the University of Missouri's 19th Annual Conference on Trace Substances in Environmental Health*, pp. 193-208, Jun. 1985.
Rodan, G. et al., Therapeutic Approaches to Bone Diseases, *Science*, 289: 1508-14, Sep. 1, 2000.

* cited by examiner

COMPOSITIONS COMPRISING STRONTIUM AND VITAMIN D AND USES THEREOF

FIELD OF INVENTION

The present invention relates to pharmaceutical compositions for the manufacture of medicaments useful for treatment of cartilage and bone disorders. The composition according to the invention comprises at least two strontium salts and may further comprise secondary active ingredients such as a vitamin D compound. The compositions may be used in different types of formulations. The compositions comprise a large amount of strontium relative to the total amount of strontium salts and are therefore very useful for the manufacture of medicaments for the treatment of bone disease and disorders.

BACKGROUND OF INVENTION

Bone material is continuously removed by osteoclasts and replaced with new bone material formed by osteoblasts.

This continuous process is highly regulated, i.e. the functioning of osteoclasts and osteoblasts are linked such that total amount of bone is constant e.g. the same amount of bone is formed as is being removed.

Osteoblasts synthesise the collagenous precursors of bone matrix and also regulate its mineralization. The activities of the osteoblasts meet the requirements of skeletal growth and matrix and also regulate its maintenance and mechanical function.

These activities are thought to be influenced by various factors, such as hormones, growth factors, physical activity and other stimuli. Osteoblasts are thought to have receptors for parathyroid hormone and estrogen. Ostoeclasts adhere to the surface of bone undergoing resorption and are thought to be activated by some form of signal from osteoblasts.

Inappropriate regulation of bone re- and degeneration can lead to bone disorders, or metabolic bone diseases. Examples of such diseases are osteoporosis, including post menopausal osteoporosis, Paget's disease and rickets.

Other causes or examples of bone diseases include corticosteroid excess from Cushing's syndrome, hyperthyroidism, hyperparathyroidism, being confined to a bed and bone cancers.

A relative increase in osteoclastic activity, for example, may cause a reduction in bone density and mass, as seen in osteoporosis. Osteoporosis is characterised by a general loss of bone density. Thinning and weakening of the bones leads to increased fracturing from minimal trauma. Osteoporosis may be either a primary disease or secondary to another disease or other diseases.

Osteoporosis is the most common of the metabolic bone diseases and approximately every third women and every $8^{th}$ man suffers from osteoporosis. Post-menopausal osteoporosis is currently the most common form of osteoporosis. The most prevalent fracturing in post-menopausal osteoporosis is of the wrist and spine. Senile osteoporosis afflicts elderly patients of either sex and younger individuals occasionally suffer from osteoporosis. Senile osteoporosis, is characterised by a higher than average fracturing of the femur.

Oestrogen deficiency has been considered to be a major cause of post-menopausal osteoporosis. Indeed steroids including oestrogen have been used as therapeutic agents supplemented with calcium supplements and bisphosphonates. This treatment resulted in many side-effects, such as weight gain (infiltration of fluid—oedema), nausea, vomiting, headache, bleedings from the uterine (cervix) mucous membrane and increased risk of blood clots. Furthermore the reports of the last years have demonstrated that the oestrogen treatment of postmenopausal osteoporosis have caused breast cancer. Thus the treatment of bone disorders including osteoporosis should preferably be improved to avoid or minimise these side-effects and increase the benefits of treatment.

SUMMARY OF INVENTION

The invention relates to a pharmaceutical composition for the manufacture of a medicament for treatment of bone disease. The medicament improves the treatment of bone disease and disorders as the medicament have less side-effects and improved effects of treatment due to a high content, a high solubility and a high availability of the active components.

The invention relates to a pharmaceutical composition comprising at least two strontium salt. The composition may further comprise at least one Vitamin D compound.

A further aspect of the invention relates to the use of a pharmaceutical composition according to the invention for the manufacture of a medicament.

The invention further relates to use of a pharmaceutical composition according to the invention for the manufacture of a medicament for treatment or prevention of cartilage- and bone diseases/disorders.

An aspect of the invention relates to a method of treatment comprising administering to a subject a pharmaceutically effective amount of the pharmaceutical composition or the medicament according to the invention.

The invention further relates to a kit of part comprising;
 i. a medicament comprising at least two strontium salt and
 ii. a medicament comprising at least one calcium salt
    wherein the compositions i. and ii. are discrete units

DETAILED DESCRIPTION OF THE INVENTION

The application relates to a pharmaceutical composition for the manufacture of a medicament, and particularly for the prevention or treatment of cartilage- and bone disorders. The medicament of the invention has been found to be surprisingly efficient for alleviating symptoms of bone disorders. The medicament is more effective and the use is accompanied by fewer side effects than previously described medicaments for treatment of bone disorders. As the medicament is unrelated to steroids used for treatment of osteoporosis, treatment using the medicament according to the invention is free of the side effects associated with hormone treatment.

Without being bound by the theory it is believed that coordinated administration of strontium and/or vitamin D and/or calcium, contributes to the improved effect of the medicament. The coordinated administration of strontium and/or vitamin D and/or calcium may sensitize the bone tissue for absorption of calcium whereby the beneficial effect on bone tissue is obtained.

Thus strontium and vitamin D are preferably administered separately from calcium, whereby strontium (and vitamin D) stimulates and primes calcium absorption and bone formation. Strontium (and vitamin D) may stimulate bone formation and absorption of calcium, including calcium obtained by food products as well as calcium obtained from medicaments and dietary supplements.

Calcium

Calcium is needed for various functions in the body including maintaining of bone tissue. Especially dietary products are rich in calcium that can be easily absorbed by the body. Other products such as vegetables also comprise calcium, thus calcium supply may be increased by altering the diet of the subject. In situations where the diet does not supply the body with enough calcium or in situations where the body is not capable of using the calcium in the diet, supplements with calcium may be required.

Strontium

Strontium is, like calcium, an alkaline earth metal, and as other alkaline earth elements strontium has an oxidation number of +2 making it very reactive. Four stable isotope of strontium exists, 84, 86, 87 and 88, the latter being the most prevalent. The radioactive isotopes 89 and 90 have previously acquired considerable interest but due to their toxicity these isotopes are not relevant for the invention.

Due to the chemical similarities of calcium and strontium both compounds readily form salts with similar anionic groups. Strontium is present in small amount in normal diet, and in most products comprising calcium due to the similarities of the two elements.

The invention relates to the finding that for the treatment of bone disorders it is advantageous to coordinate administration of strontium, vitamin D and calcium to stimulate calcium uptake and to assure that calcium is available for rebuilding of the bones or preventing further loss of bone tissue and/or bone density. For patients suffering from bone disorders or bone diseases the amount of strontium, vitamin D and calcium obtained from the food is not adequate and ordinary food supplements does not provide suitable amounts of the relevant compound.

Vitamin D Compound

Vitamin $D_3$ plays an essential role in the metabolism of calcium and phosphorus in the body. A plentiful supply of 7-dehydrocholesterol, the precursor of vitamin $D_3$, exists in human skin and needs only to be activated by a moderate amount of ultraviolet light. Vitamin D deficiencies can be compensated by the intake of food additives of Vitamin $D_2$ (found in irradiated yeast and used in some commercial preparations of the vitamin) or vitamin $D_3$ (found in fish liver oils and in fortified milk) or by exposure to ultraviolet light.

The group of compounds classified as D vitamins consists of to two fat-soluble compounds; vitamin $D_2$ (calciferol) and vitamin $D_3$ (cholecalciferol). Cholecalciferol is following converted to 25-hydroxycholecalciferol in the liver, which is subsequently, in the kidney, altered to 1,25 dihydroxycholecalciferol, the two latter forms of vitamin $D_3$ being five and ten times more effective, respectively, in terms of bioavailability than cholecalciferol it self.

Strontium Composition

The invention is based on the improved effect of using a strontium composition comprising at least two strontium salts and the effect of coordinated administration of strontium and/or vitamin D and/or calcium.

Strontium Salt(s)

In one embodiment the invention relates to a strontium composition comprising at least one strontium salt. The composition may be used for the manufacture of a medicament.

The amount of strontium obtained in 1 gram of strontium salt depends on the molecular weight of the compound, relative to the number of strontium molecules therein, thus a salt with low molecular weight per strontium molecule maybe preferred.

This may be expressed as the effective ratio of the salt. The effective ration $(R_e)$ may be defined as, $$R_e = \frac{\text{Strontium(mg)}}{\text{Stontiumsalt(mg)}}.$$

The higher effective ratio the smaller amount of the salt is required. As a relatively large amount of the active ingredient is required a strontium salt with a high effective ratio is preferred.

It is preferred that the $R_e$ of the strontium salt comprised by the strontium composition is more than 0.20, or more than 0.25 or 0.30, such as more than 0.31 such as more than 0.32, such as more than 0.33, such as more than 0.34, such as more than 0.36, such as more than 0.38 more preferably more than 0.40, or such as more than 0.42, such as more than 0.44 such as more than 0.46, such as more than 0.50, such as more than 0.52, such as more than 0.54, such as more than 0.56, such as more than 0.58 or such as more than 0.60.

In an embodiment the $R_e$ of the strontium salt comprised by the strontium composition is more than 0.35 preferably more than 0.40 and most preferably at least 0.45 or 0.5.

In one embodiment the at least one strontium salt is selected from the group of; strontium camphorate, strontium carbonate, strontium chloride, strontium citrate, strontium ethanesulfonate, strontium fumarate, strontium gluconate, strontium lactate, strontium malate, strontium maleate, strontium malonate, strontium methanesulfonate, strontium nitrate, strontium oxalate, strontium phosphate, strontium silicate, strontium succinate, strontium sulphate and strontium tartrate.

In a second embodiment the at least one strontium salt(s) is selected from the group of; strontium chlorides, strontium carbonate and strontium silicates Thus in a third embodiment a strontium silicates may be used for the invention namely, $SrSiO_2$ and $SrSiO_4$.

In a fourth preferred embodiment the strontium salt is a strontium chloride selected from the group of $SrCl_2$, $SrCl_2.2.H_2O$, $SrCl_2.6.H_2O$ differing in the extent of hydration. More preferably, the strontium salt is strontium chloride hexahydrate ($SrCl_2.6.H_2O$).

The high $R_e$ of strontium carbonate makes it a preferred salt as low amounts of the salt provide high amounts of the active ingredient. Thus, in a fifth preferred embodiment the strontium salt is strontium carbonate.

The invention especially relates to the finding that improved strontium compositions may be formulated using at least two strontium salts.

The solubility or availability of strontium in the stomach may be improved by combining two or more strontium salts. Thus in an embodiment the strontium composition comprises at least tow strontium salts or such three strontium salts, or more than three strontium salts.

The effective ratio $(R_e)$ described above may also be considered in relation to compositions comprising at least two strontium salts. Then the ratio is calculated as the total weight of strontium divided by the total weight of the at least two strontium salts (' and ").

$$R_e = \frac{\text{Strontium(mg)}}{\text{Stontiumsalt}'(\text{mg}) + \text{Stontiumsalt}''(\text{mg})}.$$

It is preferred that the $R_e$ of the at least two strontium salts is more than 0.30, such as more than 0.31 such as more than 0.32, such as more than 0.33, such as more than 0.34, such as more than 0.36, such as more than 0.38, such as more than 0.40, or such as more than 0.42, such as more than 0.44 such as more than 0.46, such as more than 0.50, such as more than 0.52, such as more than 0.54, such as more than 0.56, such as more than 0.58.

In an embodiment the $R_e$ of the at least two strontium salts is 0.30-1.00, such as 0.35-0.80, such as 0.40-0.59, preferably 0.46-0.58 or more preferably 0.50-0.57.

In another embodiment the $R_e$ of the strontium salt comprised by the strontium composition is more than 0.35 preferably more than 0.40 and most preferably at least 0.45 or 0.5.

The combination of at least two salts may further serve to optimize the effect of the composition and/or minimize undesirable effect of the compounds used. For example high intake of certain compounds, such as carbonates, may alter the pH in the stomach and intestine and thereby affect the uptake and secretion of other compounds in an unfavourable way. In alternative embodiments this may be an advantage as carbonate may neutralize the gastric juice, this may be particular favourable in situation of acidity of the stomach or acid indigestion.

By the combination of two ore more strontium salts the desired effect may be obtained.

The at least two strontium salt may be selected from the group of; strontium camphorate, strontium carbonate, strontium chloride, strontium citrate, strontium ethanesulfonate strontium fumarate, strontium gluconate, strontium lactate, strontium malate, strontium maleate, strontium malonate, strontium methanesulfonate, strontium nitrate, strontium oxalate, strontium phosphate, strontium silicate, strontium succinate, strontium sulphate and strontium tartrate.

Preferably the at lest two strontium salt are selected from the group of strontium carbonate, strontium chlorides or strontium silicates More preferably the at least two strontium salts are strontium carbonate and a strontium chloride, such as strontium carbonate and especially strontium chloride hexahydrate.

It is believed strontium chloride has a positive effect on the ability of the composition to form stable tablets. Especially strontium chloride hexa-hydrate enables easy humidification of the composition and thereby the formation of a mixture suitable for tablet pressing.

With out being bound by the theory, it is further believed that strontium chloride, especially strontium chloride hexahydrate stimulates the solubilisation of the second strontium salts in the acid environment in the stomach. Thereby strontium chloride enhances the effect of the other strontium salt(s).

The high $R_e$ of strontium carbonate makes it a preferred salt as low amounts of the salt provide high amounts of the active ingredient.

The strontium composition according to the invention may comprise the two strontium salts in different percentage. Thus, strontium carbonate may contribute with 1-99.95% of the total amount of strontium comprised by the composition.

In an embodiment the strontium composition comprises at least 50% strontium carbonate. The composition may preferably comprise more strontium in the form of strontium carbonate than in the form of strontium chloride, with respect to molar percentages. In preferred embodiments the compositions comprise such as 55-99.95% of strontium in the form of strontium carbonate and 0.05 to 45% strontium in the form of strontium chloride, such as 60-95% strontium in the form of strontium carbonate and 5-40% strontium in the form of strontium chloride, or such as 70-90% strontium in the form of strontium carbonate and 10-30% strontium in the form of strontium chloride, or such as 75% strontium in the form of strontium carbonate and 25% strontium in the form of strontium chloride.

In an efficient pharmaceutical composition the amount of strontium chloride contribute with such as at least 0.05% of the strontium of the composition in other embodiments strontium chloride contribute with at least 0.1%, such as 1%, such as at least 5 or 10%, even such as at least 15 or 20% of strontium is contributed by strontium chloride. In specific embodiments strontium chloride contribute with at least 25%, such as 30% or alternatively such as 40 or 50% of the strontium of the composition.

The increased effect of the strontium composition further relates to a high solubility of the composition.

Thus the strontium salt(s) according to the invention should be readily dissolvable in water or the acidic environment of the stomach. The pH of the stomach is 4 although food intake may reduce the pH from 4 to 2.

The solubility of the strontium composition is important for the availability of strontium ions. It is further important to evaluate the solubility velocity of the strontium salt(s) to ensure that the active compound is available with the right timing after administration.

The solubility velocity of the strontium salt(s) may be measured by any method known in the art. The solubility velocity of $SrCO_3$ and $SrCL_2$ and mixtures thereof was measured using Inductively Coupled Plasma-Mass Spectrometry (ICP-MS) as described in example 10.

Secondary Active Ingredients

An improved effect of the pharmaceutical composition is achieved by the coordinated administration of strontium and/or vitamin D and/or calcium. The secondary active ingredients may be administered separately, sequentially and/or simultaneously with the strontium composition. Thus the secondary active ingredients may be administered as a separate medicament or together with strontium in a combined medicament.

In one embodiment the invention relates to a composition comprising at least two strontium salt and one or more secondary active ingredients.

The metabolism of calcium is regulated by vitamin D, and the invention further describe that improved treatment of cartilage and bone disorders by coordinated administration of strontium with a vitamin D compound. Vitamin D compound may be administered separately, sequentially and/or simultaneously with the strontium composition. Thus, according to the invention the Vitamin D compound maybe comprised by a separate medicament and thereby administered separately or sequentially from the strontium composition or administered simultaneous with strontium in a combined medicament.

According to the invention the strontium composition may comprise any vitamin D compound suitable for the manufacturing of a medicament. The vitamin D compound(s) may be one or more of the naturally occurring Vitamin $D_2$ and $D_3$ compounds, one or more vitamin $D_2$ and $D_3$ analogs or any synthetic alternative of vitamin D capable of assisting metabolism of calcium and phosphate in the body. In particular a compound with the ability to increase absorption of calcium is preferred.

In one embodiment the pharmaceutical composition comprise one or more vitamin D analogs. In a second preferred embodiment the pharmaceutical composition comprise vitamin $D_2$ in a form suitable for preparation of a medicament. In a third preferred embodiment the pharmaceutical composition comprises vitamin $D_3$ in a form suitable for preparation of a medicament. In a preferred embodiment the pharmaceutical composition comprises vitamin $D_3$ or a vitamin $D_3$ analog, most preferably vitamin $D_3$.

The success of treatment of bone disorders is increased by coordinated administration of calcium. Thus according to the invention calcium maybe comprised by a separate medicament and thereby administered separately or sequentially from the strontium composition. Thus for optimal benefit, the pharmaceutical composition should not comprise large amount of calcium. With out being bound by the theory it is believed that the effect of strontium is neutralised if the composition comprises more calcium than strontium. Therefore the weight ratio of strontium to calcium should not be less than 1. It is further considered that an increase effect is obtained if the amount of strontium exceeds the amount of calcium. Thus it is preferred that the weight ratio of strontium to calcium is more than 1, such as more than 1.2, or such as more than 1.5, or such as more than 1.8, or such as more than 2, or such as more than 5, or such as more than 10, or such as more than 15, or such as more than 20, or such as more than 25.

It is most preferred that the pharmaceutical composition comprising strontium comprises an insignificant amount of calcium.

Although, the composition comprising strontium may comprise only modest amounts of calcium, the invention further relates to a second pharmaceutical composition comprising calcium, for the coordinated administration with the strontium comprising medicament. The medicament may comprise calcium in any form suitable for the preparation of a medicament.

Calcium compounds useful for the preparation of a pharmaceutical composition include the following compounds; calcium acetate, calcium carbonate, calcium chloride, calcium citrate, calcium gluconate (or calcium glubionate), calcium gluceptate, calcium glycerophosphate, calcium lactate, calcium lactate-gluconate, di-basic or tri-basic calcium phosphate.

According to the invention the calcium composition preferably comprise calcium in the form of a calcium salt, such as calcium carbonate, di-basic calcium phosphate ($CaHPO_4$) or tri-basic calcium phosphate ($Ca_3(PO_4)_3/Ca_5(OH)(PO_4)_3$) or a chelated calcium compound, such as calcium citrate ($Ca_3(C_6H_5O_7)_2.4H_2O$) or calcium lactate ($CaCH_3CHOHCOO)_2 5.H_2O$).

According to the invention the calcium composition may comprise calcium in a form combined with other substances, such as calcium lactate or calcium gluconate.

In one preferred embodiment the calcium composition comprise a calcium salt selected from the group of calcium carbonate, calcium phosphate and calcium citrate.

In a second embodiment the calcium composition comprises the calcium salt calcium citrate.

In a third preferred embodiment the calcium composition comprises the calcium salt calcium carbonate.

Other components able to improve the treatment may be added to the pharmaceutical composition according to the composition.

To further strength the bones additional compounds may be added. Such compounds may, for example be selected from other metals such as silicon.

In an embodiment the composition according to the invention further comprise silicon.

The invention relates to the finding that the most effective treatment is obtained by coordinated administration of at least one strontium salt, Vitamin D and a Calcium salt. The three components may be administered separately, sequentially and/or simultaneously. Most importantly, the calcium salt should be administer separately from the at least one strontium salt and the vitamin D compound.

Pharmaceutical Composition

Pharmaceutical compositions of the present invention may be prepared by conventional techniques, e.g. as described in Remington: The Science and Practice of Pharmacy 1995, edited by E. W. Martin, Mack Publishing Company, 19th edition, Easton, Pa. Standard test of mass variant and disintegration time may be measured as described in European Pharmacopoeia (Ph. Eur.)

An aspect of the invention relates to a pharmaceutical composition comprising at least two strontium salts. In further embodiment the invention relates to a pharmaceutical composition with any of the characteristics of the strontium composition described herein above.

With out being bound by the theory it is believed that a composition with favourable pharmacokinetic characteristics is obtained by the combination of at least two strontium salts, such as strontium carbonate and strontium chloride, especially strontium chloride hexa-hydrate.

The medicament may be prepared for any suitable form of administration, in particular oral administration.

Oral administration is a preferred mode of administration of medicaments to be absorbed in the gastro intestinal tract. Solid tablet and capsules of the medicament are swallowed and dissolves following in the stomach and intestine. The active ingredient(s) is/are mostly absorbed in the small intestine by an absorptive mucosal lining the intestine. Liquid medicaments or alternatively solid medicaments dissolved prior to use may be swallowed as a solution, whereby the medicament enters the stomach and the active ingredients may subsequently be absorbed in the gastrointestinal tract mainly the small intestine. According to the invention oral administration relates to the entrance of a medicament in to the gastrointestinal system by swallowing. Depending on the composition of the medicament the active ingredients can be absorbed in the stomach or during the passage though the gastro intestinal tract. The active ingredient(s) transfers to the blood circulation and reaches its place of action via the blood circulation.

In a preferred embodiment the medicament is for oral administration

The medicament of the present invention may be formulated for a wide variety of oral administration dosage forms. The medicament comprises at least two strontium salts and suitable pharmaceutically acceptable carriers or excipients, which can be either solid or liquid.

For oral administration, such excipients include pharmaceutical grades of mannitol, lactose, starch, magnesium stearate, sodium saccharine, talcum, silicon dioxide, cellulose (preferably micro crystal), polyvidon, glucose, gelatin, sucrose, ultramyl, magnesium carbonate, and the like, preferably talcum and silicon dioxide.

In an embodiment mannitol is preferred, further polyvidon (Poly (1-vinyl-2-pyrrolidon)) and magnesium sterate may be preferred. In a further embodiment it is preferred that the composition comprises ultramyl.

In powders, the carrier is a finely divided solid which is mixed with the finely divided active ingredients of the invention. In tablets, the active ingredients of the invention is mixed with a carrier having the necessary binding capacity in suitable proportions and compacted in the shape and size desired. Powders and tablets preferably contain from one to about seventy percent of the composition according to the invention. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the composition of the invention with encapsulating material as carrier providing a capsule in which composition of the invention, with or without carriers, is surrounded by a carrier, which is in association with it. Similarly, cachets and lozenges are included. Tablets, powders, capsules, pills, cachets, and lozenges are suitable for oral administration.

Solid administration form preparations include powders, tablets, pills, capsules, cachets, suppositories, and dispersible granules. Solid administration form preparations may include one or more substances which may act as colorants, flavouring agents, stabilizers, buffers, artificial and natural sweeteners, dispersants, thickeners, solubilizing agents, diluents, lubricants, suspending agents, binders, preservatives, wetting agents, tablet disintegrating agents and encapsulating material.

The medicament may according to the invention be administered as tablets, capsules, powders, dissolvable tablets or powders or by any other form suitable for oral administration.

A favour preparation form is tablets. The manufacturing method may be entirely conventional, e.g. formation of a granulate intermediate containing some or all of the milled components, followed by optionally blending with the other components and then pressing into tablets. A pharmaceutical composition capable of forming a stable tablet using tablet standard manufacturing method as described below is preferred. The stability of tablets may be evaluated based on methods know in the art. In one preferred embodiment the medicament is a tablet.

It is further contemplated that the combination of at least two strontium salts may enhances the ability of the composition to be pressed as tablets. Some strontium salts does not readily form stable tablets using conventional pharmaceutical excipients. In order to facilitate the formation of stable tablets at least two strontium salts are used according to the invention.

Initial trails showed difficulties in the preparation of tables as some tablets decomposed with in few days, such as 4-5 days. According to the invention the composition comprises at least two strontium salts assisting the formation of stable tablets, such as tablets not decomposing within 7 days, such as with in 2 weeks, preferably the tablets are stable for at least 3 or 4 week or more preferably 2 months. Most preferably the tablets are stable for at least 3 months, such as at least 4 or 5 months preferably at least 6 months. Further problems relating to the formation of homogenous tablets with equal amounts of the active ingredients was experienced. These problems may be reduced by using at least two strontium salts.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the composition of the invention in water and adding suitable colorants, flavours, stabilizing and thickening agents. Aqueous suspensions can be prepared by dispersing the finely divided composition of the invention in water with viscous material, such as natural or synthetic gums, resins, methylcellulose, sodium carboxymethylcellulose, and other well known suspending agents. Liquid form preparations include solutions, suspensions, and emulsions, and may contain, in addition to the composition of the invention, colorants, flavours, stabilizers, buffers, artificial and natural sweeteners, dispersants, thickeners, solubilizing agents, and the like.

According to the invention the medicament may be administered as drops. Drops may comprise sterile or non-sterile aqueous or oil solutions or suspensions, and may be prepared by dissolving the composition in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration, such a preparation may be dissolvable tablets or dissolvable powders. Such liquid forms include solutions, suspensions, and emulsions. These preparations may contain, in addition to the active ingredients of the invention, colorants, flavours, stabilizers, buffers, artificial and natural sweeteners, dispersants, thickeners, solubilizing agents, and the like.

In a second preferred embodiment the medicament is a dissolvable tablet.

In third preferred embodiment the medicament is a dissolvable powder.

Liquid preparations may further be a drink, such as a fruit juice, cacao milk or protein/vitamin compositions comprising at least one strontium salt, such as at least two strontium salts. Especially elder people frequently have problems swallowing tablets or other sort of medicine and may prefer drinks with more favourable tastes. It is preferred that the strontium salt or salts does not change the flavour of the drink in an untolerateable way. It is preferred to use drinks with a strong flavour to cover the taste of the strontium salts. In general the taste of strontium chloride is more offensive as to the taste of strontium carbonate and other strontium salt(s), thus the molar ratio of strontium chloride is preferably below 1, such as below 0.75, 0.5 or 0.25. The amount of added strontium salt(s) should be adjusted according to needs.

Solubilizing Agents

Solutions are favoured over suspensions for oral administration, since drugs in solution are more rapidly absorbed. Solutions are also often more acceptable to patients, in terms of palatability. It has been proposed to prepare dry effervescent formulations of medicaments in which, on addition to water (or other liquid), the medicament is dispersed in the water by the effervescing action and dissolves either as a result of the agitation or by interaction with components of the formulation.

To help the solubilization of a preparation a solubilizing agent may be included in the medicament. The solubilizing agent may be an effervescent couple which comprises an acid component and an alkaline component (a carbonate or a bicarbonate), which generates carbon dioxide on contact with water. The alkaline component of the couple is preferably present in excess of the stoichiometric equivalent of the acid component.

The acid and the alkali are the components which provide the effervescence and the disintegration of the tablet or powder as it is brought into contact with water. As acidic component citric acid both in the hydrated and anhydrous forms may be used, but other edible acids like tartaric, fumaric, adipic, malic acid can be used as well.

The carbonate, which represents the source of carbon dioxide which generates the effervescence, generally is a water-soluble alkaline carbonate such as potassium or calcium (bi)carbonate, sodium carbonate, or sodium glycine carbonate. The choice of the carbonate is very important since, besides provoking the effervescence, it can influence the robustness of the medicament. Sodium bicarbonate is one of the most used carbonate because it is very soluble and of low cost. Alternatively, modified sodium bicarbonate can be used, obtained by heating common sodium bicarbonate in order to convert the surface of its particles to sodium carbonate thereby increasing its stability.

The effervescent couple is provided in a sufficient amount to rapidly disperse and assist dissolution of the components of the formulation.

In an embodiment of the pharmaceutical composition or medicament according to the invention comprise one or more solubilizing agent(s)

The solubilizing agent(s) of the invention serve to enhance the solubility of the strontium salt and thereby to enhance the absorption of the strontium ion ($Sr^{2+}$) and thereby increase the amount of strontium entering the blood circulation.

The solubilizing agent(s) may be selected from the group of; ammonium carbonate and sodium carbonate.

Ammonium carbonate ($(NH_4)_2CO_3$) or more precisely $CH_2O_3.xNH_3$ as ammonium carbonate consists of ammonium bicarbonate ($CH_5NO_3$) and ammonium carbamate ($CH_6N_2O_2$) in varying proportions.

In an embodiment a solubilizing agent is ammonium carbonate.

In an embodiment the ammonium carbonate have approximately equal amounts of each component $CH_6N_2O_2$ and $CH_5NO_3$.

In an embodiment the ammonium carbonate have more $CH_6N_2O_2$ than $CH_5NO_3$.

In an embodiment the ammonium carbonate have less $CH_6N_2O_2$ than $CH_5NO_3$.

Sodium carbonate exists in a non-hydrated form and in a hydrated form comprising 10 water molecules associated with each sodium carbonate molecule. This enables the compound to dissolve quickly in water.

In an embodiment the solubilizing agent is sodium carbonate.

In an embodiment the sodium carbonate is sodium carbonate decahydrat ($Na_2CO_3.1 0.H_2O$).

In an embodiment the solubilizing agent is an effervescent couple preferably based on citric acid and sodium bicarbonate ($NaHCO_3$) or sodium glycine carbonate.

Lubricants

Tablets may contain conventional water-soluble lubricants such as sodium lauryl sulphate or sodium benzoate, typically up to around 7.5% or less. Alternatively tablets may be made using external lubrication on liquid-lubricated presses or on double-sided presses where solid lubricant placebo compacts containing, for example, magnesium stearate are made on one side, continuously pre-lubricating the dies.

Buffers

The pharmaceutical composition and medicament according to the invention may comprise one or more buffers useful to stabilize/neutralise pH. An example of such a buffer is ammonium chloride or citric acid. Other buffers may comprise acetate, carbonate, bicarbonate, phosphate, citrate, tris or hepes.

Encapsulating Material

The medicaments may comprise an encapsulating material surrounding the medicament. The encapsulating material may be a coating on the surface of the medicament providing the active compounds with a surface suitable for oral administration, further the coating may prevent that the active compounds are release immediately by contact with salvage in the mouth. The encapsulating material may thereby serve to postpone release of the active compounds until a specific area of the gastrointestinal system have been reached. It may be an advantage to prevent release of the active compounds in the stomach, thus the active compounds may be encapsulated until the intestine has been reached. In an embodiment hypromellose and Macrogol 6000 is used as coating agents se further below.

Controlled Release Formulations

The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.).

The various controlled release technologies cover a very broad spectrum of drug dosage forms. Controlled release technologies include, but are not limited to physical systems and chemical systems.

Physical systems include, but not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., non-erodible, erodible, environmental agent ingression, and degradable), and materials physically dispersed in non-porous, polymeric, or elastomeric matrices (e.g., non-erodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, Controlled Release Technologies: Methods, Theory and Applications, 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, rectal delivery and intrauterine delivery. All of these dosage forms may be manufactured using conventional techniques, together with the techniques discussed herein.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; get diffusion-controlled gastrointestinal delivery systems; and ion-exchange-controlled gastrointestinal delivery systems, which include cationic and anionic drugs. Additional information regarding controlled release drug delivery systems may be found in Yie W. Chien, Novel Drug Delivery Systems, 1992 (Marcel Dekker, Inc.). some of these formulations will now be discussed in more detail.

Enteric coatings may be applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue of the fact that their solubility in aqueous medium is pH-dependent, and they require conditions with a pH higher then normally encountered in the stomach.

Enteric coatings may be used to coat a solid or liquid dosage form of the compounds according to the invention. Enteric coatings promote the inventive compounds remaining physically incorporated in the dosage form for a specified period when exposed to gastric juice. Yet the enteric coatings are designed to disintegrate in intestinal fluid for ready absorption. Delay of the compounds' absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the compounds according to the invention may be contained in an enterically coated multiple-unit dosage form. In a more preferable embodiment, the dosage form of the compounds according to the invention is prepared by spray-coating granules of an compounds-enteric coating agent solid dispersion on an inert core material. These granules can result in prolonged absorption of the drug with good bioavailability.

Typical enteric coating agents include, but are not limited to, hydroxypropylmethyl-cellulose phthalate, methacrylic acid-methacrylic acid ester copolymer, polyvinyl acetate-phthalate and cellulose acetate phthalate. Akihiko Hasegawa, Application of solid dispersions of Nifedipine with enteric coating agent to prepare a sustained-release dosage form, Chem. Pharm. Bull. 33: 1615-1619 (1985). Various enteric coating materials may be selected on the basis of testing to achieve an enteric coated dosage form designed ab initio to have a preferable combination of dissolution time, coating thicknesses and diametral crushing strength. S. C. Porter et al., The Properties of Enteric Tablet Coatings Made From Polyvinyl Acetate-phthalate and Cellulose acetate Phthalate, J. Pharm. Pharmacol. 22:42p (1970). In an embodiment hypromellose and Macrogol 6000 is used as coating agents.

On occasion, the performance of an enteric coating may hinge on its permeability. S. C. Porter et al., The Permeability of Enteric Coatings and the Dissolution Rates of Coated Tablets, J. Pharm. Pharmacol. 34: 5-8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., Mechanical Properties of Dry and Wet Cellulosic and Acrylic Films Prepared from Aqueous Colloidal Polymer Dispersions used in the Coating of Solid Dosage Forms, Pharmaceutical Research, 11: 882-888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, Super Saturation Mechanism of Drugs from Solid Dispersions with Enteric Coating Agents, Chem. Pharm. Bull. 36: 4941-4950 (1998). The solid dispersions may be also called solid-state dispersions. The term "coprecipitates" may also be used to refer to those preparations obtained by the solvent methods.

Solid dispersions may be used to improve the solubility and/or dissolution rate of compounds according to the invention that may be poorly water-soluble. See generally Hiroshi Yuasa, et al., Application of the Solid Dispersion Method to the Controlled Release Medicine. III. Control of the Release Rate of Slightly Water-Soluble Medicine From Solid Dispersion Granules, Chem. Pharm. Bull. 41:397-399 (1993). The solid dispersion method was originally used to enhance the dissolution rate of slightly water-soluble medicines by dispersing the medicines into water-soluble carriers such as polyethylene glycol or polyvinylpyrrolidone, Hiroshi Yuasa, et al., Application of the Solid Dispersion Method to the Controlled Release of Medicine. IV. Precise Control of the Release Rate of a Water-Soluble Medicine by Using the Solid Dispersion Method Applying the Difference in the Molecular Weight of a Polymer, Chem. Pharm. Bull. 41:933-936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of poorly water soluble compounds according to the invention may also be increased owing to some interaction with the carriers.

Examples of carriers useful in solid dispersions according to the invention include, but are not limited to, water-soluble polymers such as polyethylene glycol, polyvinylpyrrolidone, or hydroxypropylmethyl-cellulose. Akihiko Hasegawa, Application of Solid Dispersions of Nifedipine with Enteric Coating Agent to Prepare a Sustained-release Dosaae Form, Chem. Pharm. Bull. 33:1615-1619 (1985).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may be prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved adenosine analogs may be selected such that the solution is not miscible with the melt of polyethylene glycol. The polymorphic form of the adenosine analogs may then be precipitated in the melt. Such a unique method possesses the advantages of both the melting and solvent methods. Win Loung Chiou, et al., Pharmaceutical Applications of Solid Dispersion Systems, J. Pharm. Sci. 60:1281-1301 (1971).

Another controlled release dosage form is a complex between an ion exchange resin and the compounds according to the invention. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., Sustained-released drug delivery system I: Coded ion-exchange resin systems for phenylpropanolamine and other drugs, J. Pharm. Sciences 70: 379-384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, Utilization of an Amorphous Form of a Water-Soluble GPIIb/IIIa Antagonist for Controlled Release From Biodegradable Micro spheres, Pharm. Res. 14:1146-1150 (1997), and ethyl cellulose, Yoshiyuki Koida, Studies on Dissolution Mechanism of Drugs from Ethyl Cellulose Microcapsules, Chem. Pharm. Bull. 35:1538-1545 (1987).

Other controlled release technologies that may be used in the practice of this invention are quite varied. They include SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies, Dublin, Ireland. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system, PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet. In a preferred embodiment of the invention production involves including adenosine analogs in an amorphous form together with a combination of energy, excipients, and unique processing procedures.

Once included in the desirable physical form, the resultant high energy complex may be stabilized by an absorption process that utilizes a novel polymer cross-linked technology to prevent recrystallization. The combination of the change in the physical state of the adenosine analogs according to the invention coupled with the solubilizing characteristics of the excipients employed enhances the solubility of the adenosine analogs according to the invention. The resulting absorbed amorphous drug complex granulate may be formulated with a gel-forming erodable tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant adenosine analog according to the invention throughout the gastrointestinal tract. Controlled release characteristics of the individual beads may avoid high concentration of drug being both released locally and absorbed systemically. The combination of both approaches serves to minimize the potential harm of the adenosine analog according to the invention with resultant benefits to patients.

IPDAS is composed of numerous high density controlled release beads. Each bead may be manufactured by a two step process that involves the initial production of a micromatrix with embedded adenosine analogs according to the invention and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. Adenosine analog release occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

MODAS is a drug delivery system that may be used to control the absorption of water soluble adenosine analogs according to the invention. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption and reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a micro environment within the tablet that facilitates more predictable release and absorption rates. The addition of an immediate release outer coating may allow for development of combination products.

Additionally, PRODAS may be used to deliver adenosine analogs according to the invention. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain adenosine analogs according to the invention. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract.

Packages

Tablets and dissolvable tablets are preferably conventionally packaged in protective containers such as screw cap bottles, aluminium foil sachets, plastics or metal tubes, or aluminium blister packs. Dissolvable powders or granules are preferably conventionally packaged in individual packages such as bags, sacks, sachets or saccules each containing a dose of the medicament. The bags may be made of water resistant or damp-proof materials, such as aluminium foil. It may be appropriate to incorporate a desiccant in the packages.

The packages may comprise separate strontium, vitamin D and calcium medicaments, or a combined medicament comprising strontium and vitamin D and a seperate medicament comprising calcium. Such packages may be in the form of blister packages including strontium tablets (including or excluding vitamin D) and calcium tablets side by side. Hereby the patient obtains the possibility to administer the different medicaments independently while avoiding the difficulties associated with handling multiple packages of medicaments. The packages may further include information about the timing of administration of the different medicaments.

Kit of Parts

The packages may be a kit of parts comprising the active ingredients in one or more medicament suitable for administering to the subject.

In one embodiment the invention relates to a kit of part comprising;
  i. a medicament comprising at least two strontium salt and
  ii. a medicament comprising at least one calcium salt,
    wherein the medicaments i. and ii. are discrete units.

In a second embodiment the strontium medicament comprise a vitamin D compound.

The kit of parts, according to the invention, may comprise a medicament having one or more of the characters of the pharmaceutical composition and medicament described above.

Solubility

An effective oral administered medicament should be easily dissolved. Disintegration of the medicament enhances the solubility and thus fast disintegration is important for the solubility and following absorption of the medicament. It is well experienced that for oral administered substances, that, unless the substance has an aqueous solubility above 10 mg/ml over the pH-range 1-7, potential absorption problems may occur. A solubility less than 1 mg/ml is likely to give dissolution-rate limited absorption because solubility and dissolution rate are interrelated.

The pharmaceutical composition and medicament according to the invention readily dissolve in water or in the acid environment of the stomach.

In order to evaluate a pharmaceutical composition it is important to confirm solubility of the active ingredients. As the intestine and stomach environment is acidic the solubility of pharmaceutical compositions for oral administration are preferably measured in a similar environment with a pH below 5, such as below 4 or below pH 3, preferably below pH 2.

The release of the active ingredients of the pharmaceutical composition may be measured as described in example 15 where the release of strontium from a medicament formulated as a tablet is measured. The amount of released strontium is measured after 15, 30, 45 and 60 minutes. In an embodiment the amount of released strontium is at least 40% within 45 minutes, or at least 50% is released within 45 minutes, preferably at least 55% or more preferably 60% is released within 45 minutes. In alternative embodiments at least 35% is released within 30 minutes, preferably 40%, more preferably at least 45 and most preferably 50% is released with in 30 minutes.

Disintegration

For solid medicaments disintegration increases with the surface area of the medicament and therefore enhances the solubility, thus it is preferred that the disintegration of the medicament is fast.

For easy use of a dissolvable medicament it is preferred that the medicament have a short disintegration time, thus the time from immerging the medicament in water until the solution is ready should not be long. At the same time the medicament must have a reasonably robustness that permit the medicament to be handled, shipped, and carried by patients.

The disintegration time can be characterized by either in vivo or in vitro tests. The disintegration time of the dissolvable medicament of the invention have a desirable time range of 0-300 seconds, a range of 0-240 seconds, a preferred range of 0-120 seconds, more preferable range of 1-60 seconds or 1-30 seconds or most preferred range of 0-20 seconds.

Disintegration time of coated tablets may be measured as in Ph. Eur. in water and should not exceed 60 minutes, preferably the disintegration time is at most 45 minutes such as at most 30 minutes and most preferably less than 30 minutes.

This invention describes pharmaceutical compositions and medicaments which are comprised of a highly compactable, rapidly dispersing tablet and one or more active ingredients that may be directly compressed to form rapidly dispersing tablet with practical hardness and resistance to chipping and abrasion.

The invention further relates to pharmaceutical compositions and medicaments which are comprised of highly compactable rapidly dispersing powders comprising one or more active ingredients.

Disintegration Volume of Dissolvable Medicaments

Dissolvable tablet or powder should be easily disintegrated in a volume of water (or other liquid), suitable for consumption by the patient. The solution obtained should be of a consistence, colour and taste not disfavoured by the patient. In an embodiment the disintegration volume of a dosage is less than 250 ml, such as less that 200 ml, such as less than 150 ml, such as less than 100 ml.

Dosages

The dosage requirements will vary with the particular drug composition employed, the route of administration and the particular subject being treated. Ideally, a patient to be treated by the present method will receive a pharmaceutically effective amount of the compound not exceeding the maximum tolerated dose (MTD), which is generally no higher than that required before drug resistance develops.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

The dosage may further vary depending on the treatment. For example preventive treatment and maintaining treatment may include dosages comprising approximately half the amounts of active ingredients. A period of maintaining treatment may follow a normal treatment, to maintain healthy and/or strong bones or to prevent reoccurring of the disease or disorder. Preventive treatment may be relevant for patients receiving corticosteroid treatment e.g. in rheumatism/arthritis patients. Such treatment may be for a limited period or a life long treatment.

Strontium

An effective dosage of strontium includes at least 300 mg strontium equaling 3.5 mmol of strontium. Thus the dosages of strontium should be in the amounts from 3.5 mmol to 15 mmol of the strontium salt(s).

In preferred embodiments a dosage of the medicament comprise 3.0-15 mmol of strontium or such as 4-12 mmol, or such as 5-10 mmol of strontium, or such as 6-8 mmol of strontium, or such as 6.5-7.5 mmol of strontium.

Strontium is according to the invention administered as at least two strontium salt, such as for example strontium carbonate, strontium chloride or strontium silicate.

A dosage may include various amounts of the strontium salts depending of the strontium salts comprised by the pharmaceutical composition. A dosage may comprise 0.5 g to 2.2 g of strontium carbonate, or such as 0.57 g to 2.7 g of strontium silicate or such as 0.5 to 4 g of a strontium chloride, also depending on the level of hydration.

In a preferred embodiment a dosage comprise 0.9 g to 4.0 g of strontium chloride hexahydrate.

In embodiments comprising two strontium salts a dosage may comprise various amounts of the strontium salts as described in the section related to the strontium salts.

Calcium

According to the invention a dosage of the medicament comprises 5 to 50 mmol, or such as 10 to 40 mmol, or such as 12.5 to 37.5 mmol, or such as 15 to 35 mmol, or such as 20 to 30 mmol, or such as 22.5 to 28 mmol of calcium.

In an embodiment a dosage comprise 10 to 50 mmol of calcium.

Equivalent dosage of the medicament according to the invention comprises 200 to 2000 mg of calcium, or such as 400 mg to 1600 mg, or such as 500 mg to 1500 mg, or such as 600 mg to 1400 mg, or such as 800 mg to 1200 mg, or such as 900 mg to 1100 mg calcium per dosage.

According to the invention the medicament preferably comprises 500 mg to 1500 mg calcium, or such as 750 mg to 1225 mg calcium per dosage, or such as 900 mg to 1100 mg calcium such as approximately 1000 mg calcium per dosage.

Depending on the calcium compound various amounts of the calcium salt or salts, such as 0.5 g to 5.0 g of calcium carbonate, and 0.95 g to 9.5 g of calcium citrate, and 0.8 mg to 8.5 mg of dibasic calcium phosphate dehydrate, and 0.5 g to 8 g of tri-basic calcium phosphates.

Vitamin D

The amount of the vitamin D compound may be varied depending on the needs. As mention below few subgroups of patients may not tolerate Vitamin D compounds, and thus a medicament with insignificant amounts of vitamin D may be useful. In other embodiments the medicament may comprise Vitamin D. According to the invention at least 25, such as at least 50, such as at least 100, such as at least 200, such as at least 400 IU of vitamin D should be administered pr dosage.

According to the invention up to 1000, such as up to 800, such as up to 600, such as up to 400, such as up to 200 IU of vitamin D should be administered pr dosage. As described above any compound having an effect of vitamin D suitable for the manufacturing of a medicament, including vitamin $D_2$, vitamin $D_3$ and analogs thereof may be used.

In an embodiment a dosage of the medicament comprise 100-800 IU of a vitamin D compound.

In a preferred embodiment a dosage of the medicament comprise 200-400 IU of a vitamin D compound.

In a preferred embodiment a dosage of the medicament comprise 200-400 IU or 5 to 12 microgram of vitamin $D_3$ (cholecalciferol).

The precise dosage may depend upon age, clinical evaluation, diet, nutritional status, and the availability of sunlight.

It is further contemplated that a subgroup of patients may not tolerate Vitamin D compounds. An example of such a subgroup is patients suffering from sarcoidosis or Boeck's disease, thus in such particular cases the Vitamin D compound should be omitted. Furthermore, vitamin $D_3$ (cholecalciferol) should not be administered to patients with reduced kidney function due to altered metabolism of cholecalciferol in these patients.

Bone Disorders

In appropriate regulation of bone re- and degeneration can lead to bone disorders or metabolic bone diseases resulting in weakening of the bones and following an increased rate of fractures. Included are cartilage and/or bone disease and/or conditions resulting in a dysregulation of cartilage and/or bone metabolism in a subject, such as e. g. osteoporosis, osteoarthritis, osteopetrosis, osteopenia and Paget's disease, hypercalcemia of malignancy, periodontal disease, hyperparathyroidism, periarticular erosions in rheumatoid arthritis, osteodystrophy, myositis ossificans, Bechterew's disease, malignant hypercalcemia, osteolytic lesions produced by bone metastasis, bone pain due to bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, fractures after trauma or atraumatic fracture, implant instability, need of strengthening muscle tissues and need for weight gain.

Treatment

The medicament according to the invention may be used for treatment or prevention of cartilage and bone diseases/disorders as mentioned above. Treatments of diseases disorders include reduction of the symptoms of the diseases/disorder, preventing development of a bone diseases/disorder, or prevention or inhibition of the progression of a diseases/disorder.

In one embodiment the pharmaceutical composition of the invention is used for the preparation of a medicament for treatment and prevention of cartilage or bone diseases/disorders.

In a second embodiment the pharmaceutical composition of the invention is used for the preparation of a medicament for treatment or prevention of osteoporosis.

Method of Prevention and Treatment.

An aspect of the invention relates to a method of treatment or prevention comprising administering to a subject a pharmaceutical effective amount of a medicament comprising at least two strontium salts.

In an embodiment the invention relates to a method of treatment comprising administering a pharmaceutical effective amount of a pharmaceutical composition or medicament according to the invention.

In a further embodiment the method of treatment is for the prevention or treatment of a cartilage or bone disease/disorder.

In a second embodiment the method of treatment is for the prevention or treatment of osteoporosis.

In a preferred embodiment the method of treatment include administration of 3.5-15 mmol of strontium per dosage.

The method according to the invention further include coordinated administration of medicaments according to the invention comprising at least two strontium salt and/or vitamin D and/or calcium and. By coordinated administration is meant that the medicaments may be administered separately, sequentially or simultaneously.

In an embodiment the method include administration of a medicament comprising calcium, wherein administration of calcium is separate from administration of strontium.

In an embodiment the medicament comprising strontium is administered prior, such as at least 30 minutes before, such as at least 45 minutes before, such as at least 60 minutes before, such as at least 90 minutes before, such as at least 120 minutes before, such as at least 180 minutes before, such as at least 240 minutes before, such as at least 300 minutes before, such as at least 360 minutes before the medicament comprising calcium. In preferred embodiments the medicament comprising strontium is administered at least 7 or more preferably at least 8 hours before the calcium comprising medicament.

In a second embodiment the medicament comprising strontium is administered prior, such as up to 360 minutes before, such as up to 300 minutes before, such as up to 240 minutes before, such as up to 180 minutes before, such as up to 120 minutes before, such as up to 90 minutes before, such as up to 60 minutes before, such as up to 45 minutes before, such as up to 30 minutes before the medicament comprising calcium. Preferably the strontium is administer up to 10 hours, such as 9 or 8 hours before the calcium comprising medicament.

In a further embodiment the medicament comprising strontium is administered simultaneously with a vitamin D compound either as a separate medicament or as a combined medicament.

DETAILED DESCRIPTION OF THE DRAWINGS

Figure 1:
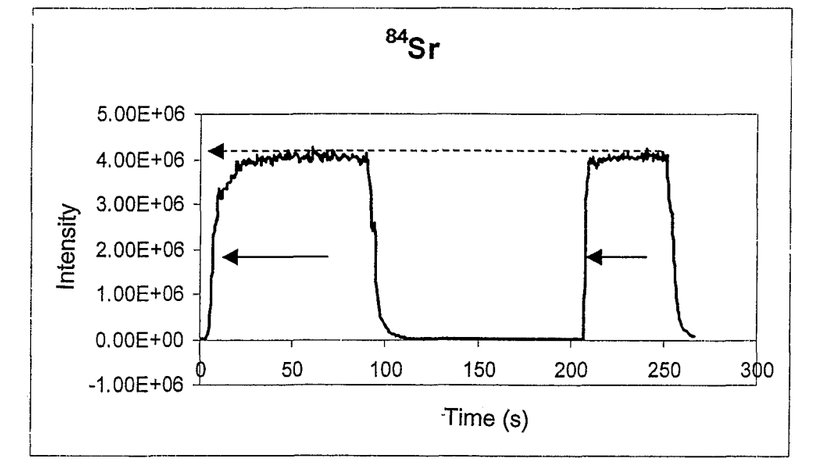
FIG. 1 ICP-MS analysis of $Sr^{84}$ in different strontium salts

FIG. 1. The $^{84}$Sr signal obtained by ICP-MS analysis of a strontium carbonate and strontium chloride composition as described in example 10.

The arrows points at the front curves and the top value used to calculate the solubility velocity.

EXAMPLES

The following examples illustrate the invention without limiting it thereto.

Example 1

100% Strontium carbonate
$R_e$=0.59
1038 g Strontium carbonate (7 mmol)

Example 2

75% Strontium carbonate
25% Strontium chloride
$R_e=0.52$
778.50 g Strontium carbonate (5.3 mmol)
469.25 g Strontium chloride (1.7 mmol)

Example 3

50% Strontium carbonate
50% Strontium chloride
$R_e=0.46$
519 g Strontium carbonate (3.5 mmol)
938.5 g Strontium chloride (3.5 mmol)

Example 4

75% Strontium chloride
25% Strontium carbonate
$R_e=0.39$
1,410 g Strontium chloride (5.3 mmol)
250 g Strontium carbonate (1.7 mmol)

Example 5

100% Strontium chloride
$R_e=0.325$
1,866 g Strontium chloride (7 mmol)

Example 6

1.33 g Strontium chloride (5 mmol)
0.74 g Strontium carbonate (5 mmol)

Example 7

1.33 g Strontium chloride hexahydrate (5 mmol)
0.74 g Strontium carbonate (5 mmol)
20 μg of vitamin $D_3$ (cholecalciferol)

Example 8

Strontium chloride solubilized by ammonium carbonate
2.66 g Strontium chloride (10 mmol)
Ammonium carbonate (solubilizing agent)

Example 9

Strontium carbonate solubilized by sodiume carbonate
1.48 g Strontium carbonate (10 mmol)
20 μg vitamin $D_3$ (cholecalciferol)
Sodium carbonate decahydrate (solubilizing agent)

Example 10

Determination of Solubility Velocity by Inductively Coupled Plasma-Mass Spectrometry (ICP-MS)

The solubility is measures as strontium signals over time using ICP-MS. Using this technique it is possible to follow multiple isotopes of the element, here, $^{84}Sr$, $^{86}Sr$, $^{87}Sr$ and $^{88}Sr$.

The measurement was performed on strontium salts as indicated in table 1, following the examples 1 to 3 here above. A hydrochloride solution (0.1 M) was added to the sample and the sample then immediately enters, by means of a peristaltic pump, the atomizer of the ICP-MS apparatus. The pump speed was 4.4 ml/min.

The hydrochloride concentration of 0.1 M equals the concentration of HCl in the stomach. The temperature of the HCl solution was 37° C.

| Experiment | Mass SrCO3 (mg) | Mass SrCl2*6H2O (mg) | Mass Sr (mg) |
|---|---|---|---|
| 1 | 1039 | 0 | 617 |
| 2A | 779.1 | 476.0 | 619 |
| 2B | 780.9 | 466.1 | 617 |
| 3 | 522.4 | 941.5 | 620 |

Results

The signal relating to the isotope 84Sr was followed. The signal obtained in experiment 3 is shown in FIG. 1.

The solubility velocity of the compound is obtained by analysing the slopes of the front curves. The first curve represents the experiment and the second curve the apparatus, thus the difference between the slopes of the two curves are used to calculate the solubility velocity by division with the top value. The solubility velocity of strontium was found not to be significantly different in the three experiments.

The solubility velocity for strontium carbonate and for strontium chloride in hydrochloride is very high. The average solubility was determent to 240+/− 165 mg Strontium per second.

Example 11

Medicament formulated as a tablet

Strontium from strontium chloride provides 0.06% of all strontium $$R_e = \frac{30000 + 20 \text{ mg}}{511255 \text{ mg}} = 0.05872$$

1000 tablets may be formulated using the following ingredients.

| Ingredients | | |
|---|---|---|
| Strontium carbonate (58.75% Sr) | 510.64 g | 3.46 mol |
| Strontium chloride (32.5% Sr) | 615, 38 mg | 2.3 mmol |
| Vitamin D3 * 100.000 IE/G | 1.1 g (+10% OD) | |
| Cellulose (microcryst.) (Ph Eur) | 52 g | |
| Mannitol (Ph Eur) | 510, 64 g | |
| Polyvidon (Ph Eur) | 25.60 | |
| Magnesium sterate (Ph Eur) | 5.50 g | |
| Tablet weigth | 1106 mg/tablet. | |
| Strontium content | 3.46 mmol/tablet | |
| For production is further use | | |
| Ethanol 96% (Ph Eur) | 230.40 g | |
| Coating | | |
| Hypromellose (Ph Eur) | 8.84 g | |
| Macrogol 600 (Ph Eur) | 883 mg | |

-continued

| For coating is further used | |
|---|---|
| Ethanol 96% (Ph Eur) | 81.37 g |
| Water (purified?) | 19.53 g |

*Vitamin D3 composition consists of (measured according to activity):

| | |
|---|---|
| Cholecalciferol (Ph Eur) | 2.9 mg |
| Gelatine (Ph Eur) | 0.26 g |
| Saccharose (Ph Eur) | 0.39 g |
| Modified starch (FCC) | 0.20 g |
| Triglycerider medium chain (Ph Eur) | 0.21 g |
| Sodium aluminium silicate (E 554) | 2.9 mg |
| Butylhydroxytoluen (Ph Eur) | 10.5 mg |
| Water | 27.6 mg |
| Total | 1104 mg |

Ph Eur (The European Pharmacopoeia)
FCC (Food Chemical codex)

Example 12

As example 11 except that the composition further comprising 2% ultramyl.

Example 13

As example 11 and 12 except that the compositions comprises 2 times the amount of Vitamin D3, e.g. 2.2 g (+10% OD).

Example 14

Quantitative Measurement of Strontium by Atomic Absorption Spectroscopy (AAS)
Wave length: 460, 7 nm
Flame: acetylen-dinitrogenoxid
Lanthane-solution: 29.3 g $La_2O_3$+50 ml konc HCL+$H_2O$ to 500 ml
Standards: strontium standard solutions of 1, 2, 3, 4, 5 ppm. as 50 ml solutions including 10 ml La-solution.

10 tablets are weighted and the average weight ($W_a$) is determined.

The tablets are crushed and 1.200 gram is weight out (in duplicates). The crushed tablet material is transferred to a 100 ml flask (in duplicates) and 10 ml $H_2O$ and 10 ml 6 M HCL is added to each flast. The suspensions are heated over a gas flame. After 30 minutes of heating $H_2O$ is added to 100 ml. The solution is filtered and a 2:100 dilution in $H_2O$ is prepared. 2 ml of this solution is added to a 50 ml flask and 10 ml of a Lanthane-solution is added and H2O is added to 50 ml.
Calculation:

$$\text{Strontium per tablet (mg)} = \frac{\text{Measured ppm} \times 50 \times 100 \times 100 \times Wa \text{ (mg)}}{\text{Weight out mass (mg)} \times 2 \times 2 \times 1000}$$

Example 15

Solubility of Strontium Tablets
Material
USP Apparatus 2, paddle, 50 rpm.
900 ml 01 N HCl
37° C.
Height 2.5 cm above bottom
Lanthane-solution: 29.3 g $La_2O_3$+50 ml konc HCL+$H_2O$ to 500 ml The determinations are made with 6 independent experiments. The tablets are submerged in 5 ml 0.1 N HCl each at 37 C., after 15 minutes a sample of 5 ml is taken from each tube, the sample is filtered immediately. The 5 ml is replaced by 0.1 N HCl, 37 C. 1 ml of the filtered sample is transferred to a 50 ml flask and 10 ml La(II) solution and 0.1 HCl to 50 ml are added. The procedure is repeated at 30, 45 and 60 minutes from the beginning of the experiment. The content of strontium is measured using atomic absorption spectroscopy (AAS) as described in example 14.
Wave length: 460, 7 nm
Flame: acetylen-dinitrogenoxid
Standards: strontium standard solutions of 1, 2, 3, 4, 5 ppm. as 50 ml solutions including 10 ml La-solution.
Calculation:

$$\text{Dissolved Strontium (\%)} = \frac{\text{Measured ppm} \times 50 \times 0.9 \times Wa \text{ (mg)} \times 100}{\text{Weight out mass (mg)} \times 1 \times 300}$$

Example 16

The solubility of the tablets described in example 11 measured as described in example 15.
Results
The percentage of dissolved strontium is given; the figures in brackets are the highest and lowest value obtained)
Dissolved strontium at 15 minutes is 32.7% (25.5-38.4).
Dissolved strontium at 30 minutes is 41.7% (36.4-49.7).
Dissolved strontium at 45 minutes is 51.6% (44.3-58.8).
Dissolved strontium at 60 minutes is 60.7% (55.0-70.7).

Example 17

Example of Tablet Comprising 3.5 mmol Strontium
463 mg strontium carbonate
93 mg strontium chloride
297 mg MCC
100 mg Mannitol
12 mg Sillicon Dioxid
5 mg Magnesium sterat Example 18

Tablets formulated as in example 11 or 17 but with different amounts of strontium carbonate and strontium chloride. Table 1 here below shows the percentage of strontium contributed by $SrCO_3$ and $SrCL_2$ and the molar amounts of each component in a tablet comprising 3.5 mol of strontium.

TABLE 1

| | $SrCO_3/SrCL_2$ (%) | $SrCO_3$ (mmol) | $SrCL_2$ (mmol) |
|---|---|---|---|
| A | 1/99 | 0.035 | 3.465 |
| B | 2/98 | 0.070 | 3.430 |
| C | 5/95 | 0.175 | 3.325 |
| D | 7/93 | 0.245 | 3.255 |
| E | 10/90 | 0.350 | 3.150 |
| F | 15/85 | 0.525 | 2.975 |
| G | 20/90 | 0.700 | 2.800 |
| H | 25/75 | 0.875 | 2.625 |
| I | 30/70 | 1.050 | 2.450 |
| J | 40/60 | 1.400 | 2.100 |
| K | 50/50 | 1.750 | 1.750 |

In further examples the compositions may further comprise the components as described in example 12 and 13.
The solubility of the tablets is analysed as in example 15.

The invention claimed is:

1. A pharmaceutical composition in the form of a tablet, a cachet, a capsule, a pill or a dissolvable tablet comprising:
   at least one strontium chloride and at least one strontium salt selected from the group consisting of strontium carbonate and strontium silicates.

2. The pharmaceutical composition according to claim 1, wherein the composition comprises strontium carbonate.

3. The composition according to claim 1, wherein the composition comprises a strontium chloride selected from the group of: $SrCl_2$, $SrCl_2\ 2.H_2O$, $SrCl_2\ 6.H_1O$.

4. The pharmaceutical composition according to claim 3, wherein the strontium chloride is $SrCl_2\ 6.H_2O$.

5. The pharmaceutical composition according to claim 1, wherein the composition comprises strontium chloride hexahydrate and strontium carbonate.

6. The pharmaceutical composition according to claim 1, wherein the composition comprises a solubilizing agent.

7. A method for treating a disease or disorder of cartilage and/or bone, said method comprising administering to a patient a composition of claim 1.

8. The method of claim 7, wherein the composition is administered orally.

9. The method of claim 7, wherein the amount of strontium released by said composition is at least 40% within 45 minutes.

10. The method of claim 7, wherein the composition is formulated as a tablet.

11. The method of claim 10, wherein the tablet is a coated tablet.

12. The method of claim 7, wherein the composition is formulated for controlled release.

13. The method of claim 7, wherein the composition is formulated as a dissolvable medicament.

14. The method of claim 7, wherein a dosage of said composition comprises 3.0-15 mmol of strontium.

15. The method according to claim 7, further comprising administration of a medicament comprising calcium, wherein administration of calcium is separate from administration of strontium.

16. A kit of parts comprising:
   i) a medicament in the form of a tablet, a cachet, a capsule, a pill or a dissolvable tablet comprising at least one strontium chloride and at least one strontium salt selected from the group consisting of: strontium carbonate and strontium silicates; and
   ii) a medicament comprising at least one calcium salt;
   wherein the compositions i) and ii) are discrete units.

17. The method of claim 7, wherein the method is for the treatment of osteoporosis.

18. The method of claim 7, wherein said composition includes at least one Vitamin D compound.

19. The method of claim 7, further comprising administering calcium to said patient.

20. The method of claim 19, wherein said calcium is contained in said composition of claim 1.

21. A pharmaceutical composition in the form of a tablet, a cachet, a capsule, a pill or a dissolvable tablet comprising at least one strontium chloride and at least one strontium salt selected from the group consisting of: strontium carbonate and strontium silicates; at least one vitamin D compound selected from the group of: vitamin $D_3$ and vitamin $D_2$; and a vehicle for the systemic delivery thereof.

22. A pharmaceutical composition in the form of a tablet, a cachet, a capsule, a pill or a dissolvable tablet comprising: strontium chloride; at least one strontium salt selected from the group consisting of: strontium carbonate and strontium silicates; at least one vitamin D compound selected from the group consisting of: vitamin $D_3$ and vitamin $D_2$; and a calcium salt.

* * * * *

UNITED STATES PATENT AND TRADEMARK OFFICE
CERTIFICATE OF CORRECTION

PATENT NO. : 8,658,206 B2
APPLICATION NO. : 11/570767
DATED : February 25, 2014
INVENTOR(S) : John Nikolaj Hvarre Christensen It is certified that error appears in the above-identified patent and that said Letters Patent is hereby corrected as shown below:

On the Title Page: Item (56) References Cited under OTHER PUBLICATIONS, line 12 (Sorbera publication): Replace "ther" with --the--;

In the Claims:

Column 27, Claim 3, line 11: Replace "$SrCl_2$, $SrCl_2\ 2.H_2O$, $SrCl_2\ 6.H_1O$" with --$SrCl_2$, $SrCl_2 \cdot 2H_2O$, $SrCl_2 \cdot 6H_2O$--;

Column 27, Claim 4, line 13: Replace "$SrCl_2\ 6.H_2O$" with --$SrCl_2 \cdot 6H_2O$--.

Signed and Sealed this
Eighth Day of July, 2014

Michelle K. Lee
*Deputy Director of the United States Patent and Trademark Office*